US011676708B2

(12) United States Patent
Guarino et al.

(10) Patent No.: US 11,676,708 B2
(45) Date of Patent: Jun. 13, 2023

(54) SYSTEMS AND METHODS FOR EFFICIENTLY MANAGING HOSPITAL OPERATING ROOMS

(71) Applicant: CCDR Group LLC, E. Bluffton, SC (US)

(72) Inventors: Richard C. Guarino, Centereach, NY (US); Damian Barker, Syosset, NY (US); Chris DiRusso, East Patchogue, NY (US)

(73) Assignee: CCDR GROUP LLC, E. Bluffton, SC (US)

( * ) Notice: Subject to any disclaimer, the term of this patent is extended or adjusted under 35 U.S.C. 154(b) by 236 days.

(21) Appl. No.: 16/408,531

(22) Filed: May 10, 2019

(65) Prior Publication Data
US 2019/0362837 A1 Nov. 28, 2019

Related U.S. Application Data

(60) Provisional application No. 62/669,535, filed on May 10, 2018.

(51) Int. Cl.
*G16H 40/20* (2018.01)
*G16H 40/60* (2018.01)
(Continued)

(52) U.S. Cl.
CPC .............. *G16H 40/20* (2018.01); *G16H 40/60* (2018.01); *G06Q 10/06* (2013.01); *G16H 40/40* (2018.01)

(58) Field of Classification Search
CPC ........ G16H 40/20; G16H 40/60; G16H 40/40; G16H 40/63; G16H 10/60; G16H 50/20;
(Continued)

(56) References Cited

U.S. PATENT DOCUMENTS

2009/0272405 A1* 11/2009 Barnhill ............... G08B 21/245
134/18
2013/0304485 A1 11/2013 Khan et al.
(Continued)

FOREIGN PATENT DOCUMENTS

EP 3173960 A1 5/2017
EP 3185190 A1 6/2017
WO WO-2018051066 A1 * 3/2018 ....... G06Q 10/06311

OTHER PUBLICATIONS

International Preliminary Report on Patentability received from the International Bureau of WIPO in connection to International Application No. PCT/US2019/031720 dated Nov. 10, 2020.
(Continued)

*Primary Examiner* — Michael Tomaszewski
*Assistant Examiner* — Shyam M Goswami
(74) *Attorney, Agent, or Firm* — Carter, DeLuca & Farrell LLP; George Likourezos

(57) ABSTRACT

The present disclosure relates to systems and methods for managing hospital operating room turnover. One exemplary method includes communicating a request associated with a task to one or more users, receiving an acceptance of the request at an acceptance time by the one or more users, determining if the acceptance is on time, starting the task at a task start time, determining if the acceptance is on time based on comparing the task start time with the start due time to determine if the task start time is earlier or equal to the task start due time, indicating task completion by one or more users, recording task completion, and communicating availability of a room.

24 Claims, 11 Drawing Sheets

(51) Int. Cl.
*G16H 40/40* (2018.01)
*G06Q 10/06* (2023.01)

(58) Field of Classification Search
CPC ............. G06Q 10/06; G06Q 10/06311; G06Q 10/063; H04L 67/10
See application file for complete search history.

(56) References Cited

U.S. PATENT DOCUMENTS

| | | |
|---|---|---|
| 2017/0149701 A1 | 5/2017 | Mancine et al. |
| 2017/0185930 A1* | 6/2017 | Perry ..................... H04W 4/80 |
| 2018/0247711 A1* | 8/2018 | Terry ..................... G16H 40/40 |
| 2019/0167829 A1* | 6/2019 | Grinstead ............... A61L 2/085 |

OTHER PUBLICATIONS

International Search Report and Written Opinion dated Jun. 28, 2019 corresponding to counterpart Int'l Patent Application PCT/US19/31720.

* cited by examiner

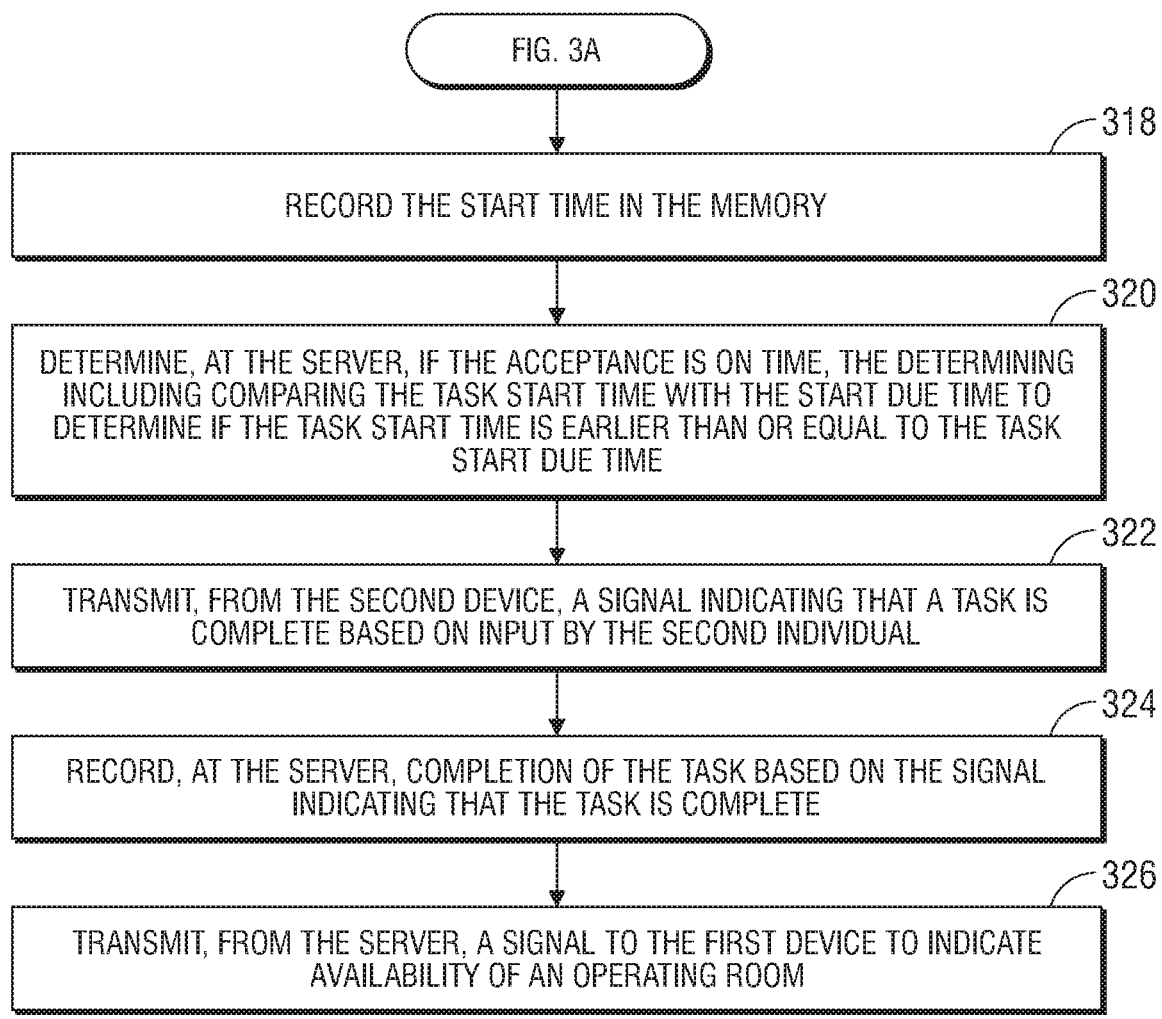

FIG. 8

| ORSTAT | Dashboard Reports Turnovers Users Teams Rooms | | Acme Hospital |

Teams | New Team

| Name | Users | Facility | Created |
|---|---|---|---|
| Housekeeping | 2 | Acme Hospital | Apr21st2018@6:05pm |
| Surgery | 1 | Acme Hospital | Apr21st2018@6:05pm |
| Anesthesiology | 1 | Acme Hospital | Apr21st2018@6:05pm |
| OR Nurse | 1 | Acme Hospital | Apr21st2018@6:05pm |
| Nurse Assistants | 2 | Acme Hospital | Apr21st2018@6:05pm |

FIG. 9

| ORSTAT | Dashboard Reports Turnovers Users Teams Rooms | | Acme Hospital |

Rooms | New Room

| Name | Facility | Created |
|---|---|---|
| 1 | Acme Hospital | Apr21st2018@6:05pm |
| 2 | Acme Hospital | Apr21st2018@6:05pm |
| 3 | Acme Hospital | Apr21st2018@6:05pm |
| 4 | Acme Hospital | Apr21st2018@6:05pm |
| 5 | Acme Hospital | Apr21st2018@6:05pm |

FIG. 10

SYSTEMS AND METHODS FOR EFFICIENTLY MANAGING HOSPITAL OPERATING ROOMS

CROSS-REFERENCE TO RELATED APPLICATION

The present application claims the benefit of and priority to U.S. Provisional Patent Application Ser. No. 62/669,535, filed on May 10, 2018, the entire contents of which are incorporated herein by reference.

TECHNICAL FIELD

The present disclosure relates to systems and methods for efficiently managing manpower resources and, more particularly, to systems and methods for managing in an efficient manner the turnover of hospital operating rooms.

SUMMARY

This disclosure relates to the managing in an efficient manner the turnover of hospital operating rooms. In accordance with aspects of the present disclosure, a computer-implemented method of managing hospital operating room turnover includes receiving, at a server including a memory, a request from a first device configured to be operated by a first individual; communicating, from the server, the request associated with the task to a second device configured to be operated by a second individual; receiving, at the second device, input associated with a first acceptance of the request at an acceptance time by the second individual; recording the first acceptance time in the memory; determining if the first acceptance is on time based on comparing the acceptance time with the acceptance due time to determine if acceptance time is earlier than or equal to the acceptance due time; communicating, from the server to the second device, a signal that the received first acceptance has been approved; determining if a second acceptance, from a third device configured to be operated by a third individual, of the task was received at a time prior to the first acceptance; in a case where the second acceptance of the task was not received, communicating, from the second device to the server, a signal indicating that the task has started and a task start time; recording the start time in the memory; determining, at the server, if the acceptance is on time, the determining including comparing the task start time with the start due time to determine if the task start time is earlier than or equal to the task start due time; transmitting, from the second device, a signal indicating that a task is complete based on input by the second individual; recording, at the server, completion of the task based on the signal indicating that the task is complete; and transmitting, from the server, a signal to the first device to indicate availability of an operating room. The request associated with a task, the request including a start due time, an acceptance due time, and a type of staff.

In an aspect of the present disclosure, the method may further include in a case where it is determined that the task is not started on time, communicating a late warning to at least one of the first device and the second device, and recording in the memory that the task is started late.

In another aspect of the present disclosure, the method may further include in a case where it is determined that the task is not accepted on time, communicating to at least the second device a late warning.

In an aspect of the present disclosure, the method may further include calculating on time performance and reporting to a display the on time performance.

In yet another aspect of the present disclosure, the method may further include calculating room performance and reporting to a display the room performance.

In a further aspect of the present disclosure, the method may further include calculating individual performance and reporting to a display the individual performance.

In an aspect of the present disclosure, the method may further include calculating a time to complete the task and reporting to a display the time to complete the task.

In a further aspect of the present disclosure, the type of staff includes at least one of housekeeping, maintenance personnel, nursing, nursing assistants, anesthesiologist, or surgeon.

In a further aspect of the present disclosure, the method may further include predicting based on a neural network whether a turnover will be late, and providing a notification of the prediction.

In a further aspect of the present disclosure, the method may further include determining a geo-location of individual staff, and providing an indication of the geo-location of the individual staff.

In accordance with aspects of the present disclosure, a non-transitory computer-readable storage medium which stores a program causing a computer to execute a computer-implemented method of managing hospital operating room turnover includes receiving, at a server including a memory, a request from a first device configured to be operated by a first individual; communicating, from the server, the request associated with the task to a second device configured to be operated by a second individual; receiving, at the second device, input associated with a first acceptance of the request at an acceptance time by the second individual; recording the first acceptance time in the memory; determining if the first acceptance is on time based on comparing the acceptance time with the acceptance due time to determine if acceptance time is earlier than or equal to the acceptance due time; communicating, from the server to the second device, a signal that the received first acceptance has been approved; determining if a second acceptance, from a third device configured to be operated by a third individual, of the task was received at a time prior to the first acceptance; in a case where the second acceptance of the task was not received, communicating, from the second device to the server, a signal indicating that the task has started and a task start time, recording the start time in the memory; determining, at the server, if the acceptance is on time, the determining including comparing the task start time with the start due time to determine if the task start time is earlier than or equal to the task start due time, transmitting; from the second device, a signal indicating that a task is complete based on input by the second individual; recording, at the server, completion of the task; and transmitting, from the server, a signal to the first device to indicate availability of an operating room. The request is associated with a task. The request includes a start due time, an acceptance due time, and a type of staff.

In a further aspect of the present disclosure, the computer-implemented method may further include in a case where it is determined that the task is not started on time, communicating a late warning to at least one of the first device and the second device, and recording in the memory that the task is started late.

In yet another aspect of the present disclosure, the computer-implemented method may further include in a case where it is determined that the task is not accepted on time, communicating to at least the second device a late warning.

In a further aspect of the present disclosure, the computer-implemented method may further include calculating on time performance and reporting to a display the on time performance.

In yet a further aspect of the present disclosure, the computer-implemented method may further include calculating room performance and reporting to a display the room performance.

In yet another aspect of the present disclosure, the computer-implemented method may further include calculating individual performance and reporting to a display the individual performance.

In a further aspect of the present disclosure, the computer-implemented method may further include calculating a time to complete the task and reporting to a display the time to complete the task.

In a further aspect of the present disclosure, the type of staff includes at least one of housekeeping, maintenance personnel, nursing, nursing assistants, anesthesiologist, or surgeon.

In a further aspect of the present disclosure, the method may further include determining a geo-location of individual staff, and providing an indication of the geo-location of the individual staff.

In accordance with aspects of the present disclosure, a system for managing hospital operating room turnover includes a first device configured to be operated by a first individual, a second device configured to be operated by a second individual, and a server. The server includes a processor, and a memory coupled to the processor and having instructions stored therein. The instructions when executed by the processor, causes the system to receive, a request from the first device, the request associated with a task, the request including a start due time, an acceptance due time, and a type of staff; communicate the request associated with the task to the second device; receive, at the second device, input associated with a first acceptance of the request at an acceptance time by the second individual; record the first acceptance time in the memory; determine if the first acceptance is on time based on comparing the acceptance time with the acceptance due time to determine if acceptance time is earlier than or equal to the acceptance due time; communicate, from the server to the second device, a signal that the received first acceptance has been approved; determine if a second acceptance, from a third device configured to be operated by a third individual, of the task was received at a time prior to the first acceptance, in a case where the second acceptance of the task was not received, communicate, from the second device to the server, a signal indicating that the task has started and a task start time; record the start time in the memory; determine if the acceptance is on time, the determining including comparing the task start time with the start due time to determine if the task start time is earlier than or equal to the task start due time; transmit, from the second device, a signal indicating that a task is complete based on input by the second individual; record completion of the task based on the signal indicating that the task is complete; and transmit a signal to the first device to indicate availability of an operating room.

In an aspect of the present disclosure, the memory has further instructions stored thereon which, when executed by the processor, causes the system to, in a case where it is determined that the task is not started on time, communicate a late warning to at least one of the first device and the second device, and recording in the memory that the task is started late.

In another aspect of the present disclosure, the memory has further instructions stored thereon which, when executed by the processor, causes the system to, in a case where it is determined that the task is not accepted on time, communicate to at least the second device a late warning.

In an aspect of the present disclosure, the memory has further instructions stored thereon which, when executed by the processor, causes the system to calculate on time performance and reporting to a display the on time performance.

In yet another aspect of the present disclosure, the memory has further instructions stored thereon which, when executed by the processor, causes the system to calculate room performance and reporting to a display the room performance.

In a further aspect of the present disclosure, the memory has further instructions stored thereon which, when executed by the processor, causes the system to calculate individual performance and reporting to a display the individual performance.

In an aspect of the present disclosure, the memory has further instructions stored thereon which, when executed by the processor, causes the system to calculate a time to complete the task and reporting to a display the time to complete the task.

In a further aspect of the present disclosure, the type of staff includes at least one of housekeeping, maintenance personnel, nursing, nursing assistants, anesthesiologist, or surgeon.

In yet another aspect of the present disclosure, the memory has further instructions stored thereon which, when executed by the processor, causes the system to predict based on a neural network whether a turnover will be late; and provide a notification of the prediction.

Further details and aspects of various embodiments of the present disclosure are described in more detail below with reference to the accompanying drawings.

BRIEF DESCRIPTION OF THE DRAWINGS

A better understanding of the features and advantages of the present disclosure will be obtained by reference to the following detailed description that sets forth illustrative embodiments, in which the principles of the present disclosure are utilized, and the accompanying drawings of which:

FIG. 3B is a continuation of the exemplary flow chart of FIG. 3A;

FIG. 8 is an exemplary user status view in accordance with aspects of the present disclosure;

FIG. 9 is an exemplary team information view in accordance with aspects of the present disclosure;

FIG. 10 is an exemplary room information view in accordance with aspects of the present disclosure;

DETAILED DESCRIPTION

Figure 1:
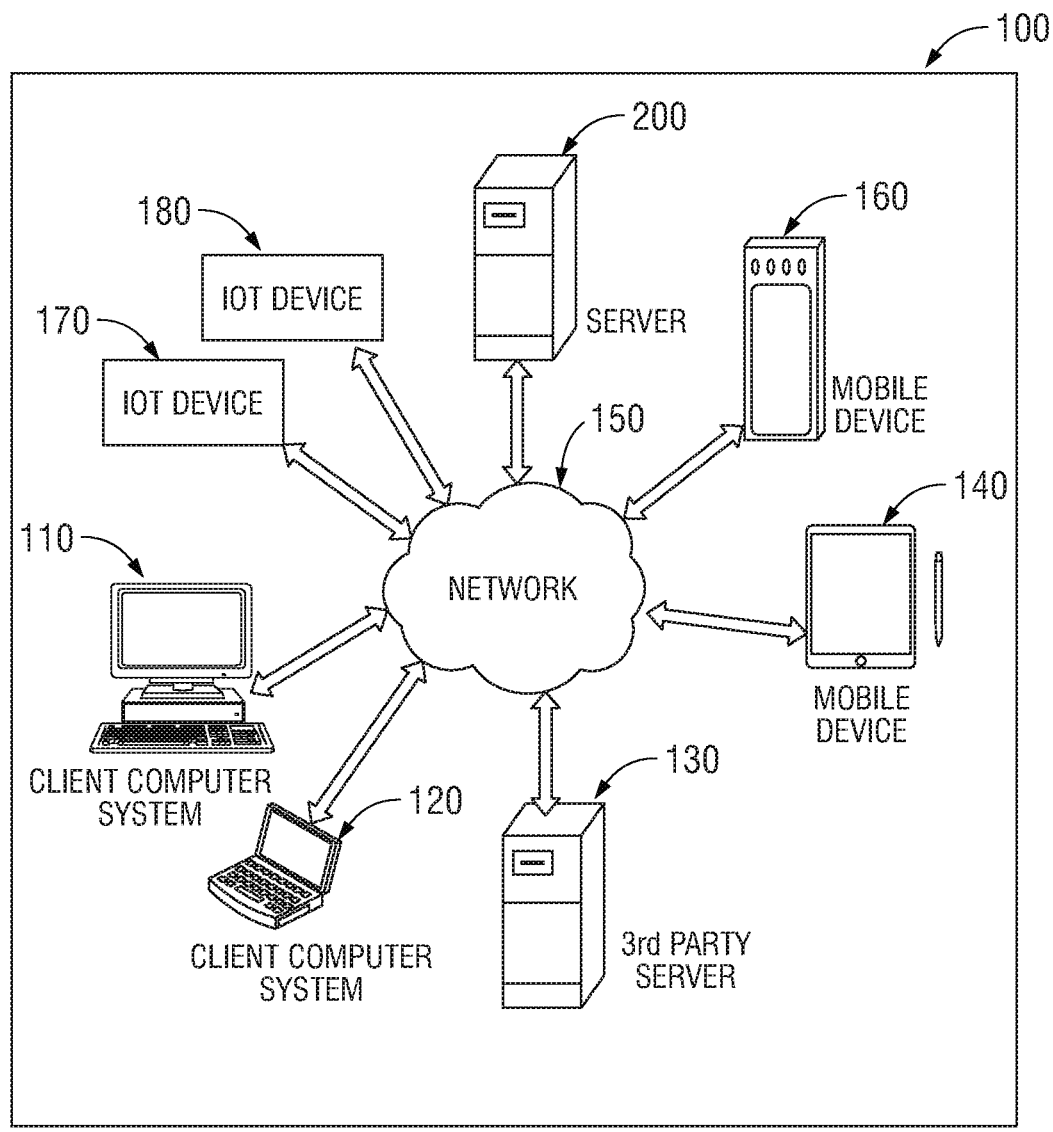
FIG. 1 is a network diagram illustration, which shows an exemplary networked environment for a computer implemented method of managing in an efficient manner the turnover of hospital operating rooms in accordance with aspects of the present disclosure.

This disclosure relates to systems and methods for the managing in an efficient manner the turnover of hospital operating rooms.

Although the present disclosure will be described in terms of specific embodiments, it will be readily apparent to those skilled in this art that various modifications, rearrangements, and substitutions may be made without departing from the spirit of the present disclosure. The scope of the present disclosure is defined by the claims appended hereto.

For purposes of promoting an understanding of the principles of the present disclosure, reference will now be made to exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

Referring to FIG. 1, there is shown an illustration of an exemplary networked environment 100 in accordance with aspects of the present disclosure. The system 100 includes one or more computers 110, 120, a network 150, a server 200, and one or more mobile device 140, 160. The mobile device(s) 140, 160, or the computers 110, 120, communicate with the server 200 across the network 150 to manage data. In one example, the server 200 may store a user's personal profile and settings. The server 200 communicates the updated task list back over the network 150 to the user mobile device 140, and a task list is displayed on the user mobile device 140.

In the illustrated embodiment, the networked environment 100 includes a third party server 130. In various embodiments, the third party server 130 can store and communicate user tasks, and the server 200 can import such user tasks from the third party server 130. In various embodiments, data, services, or applications from third party servers 130 may be used by the server 200 for scheduling operations. Such data from third party servers 130 can include, for example, a user's available time, appointments, bank balances, tags, or the weather forecast. For example, the server 200 may allow social integration, such as allowing sharing of projects, events, task etc.

The network 150 may be wired or wireless, and can utilize technologies such as WiFi, Ethernet, Internet Protocol, 3G, and/or 4G, or other communication technologies. The network 150 may include, for example, but is not limited to, a cellular network, residential broadband, satellite communications, private network, the Internet, local area network, wide area network, storage area network, campus area network, personal area network, or metropolitan area network.

The term "application" may include a computer program designed to perform particular functions, tasks, or activities for the benefit of a user. Application may refer to, for example, software running locally or remotely, as a stand-alone program or in a web browser, or other software which would be understood by one skilled in the art to be an application. An application may run on the server 200 or on a user device, including for example, on a mobile device 140 or a computer 110.

Figure 2:
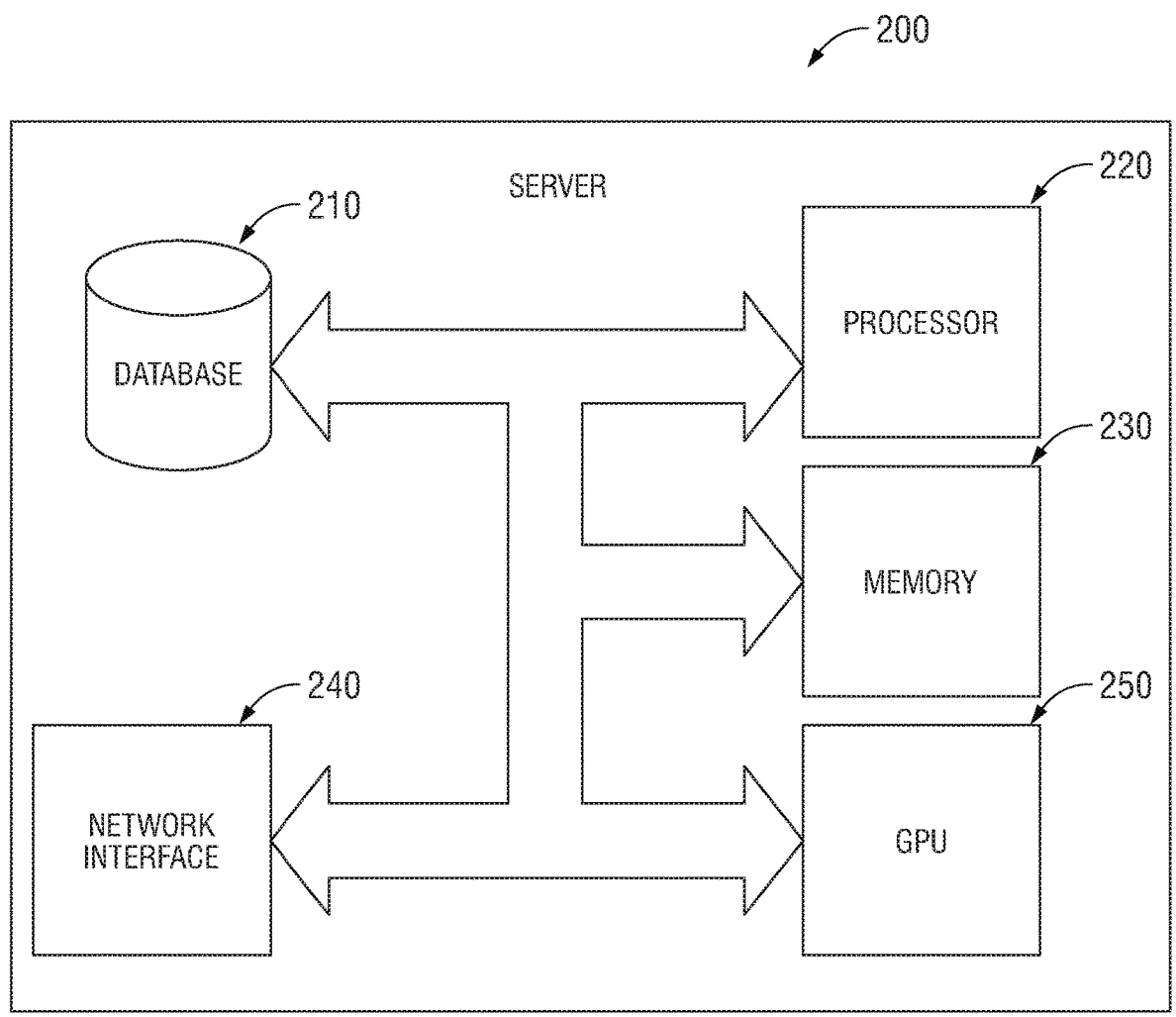
FIG. 2 is a block diagram of an exemplary server of FIG. 1 in accordance with aspects of the present disclosure.

Referring now to FIG. 2, there is shown an illustration of exemplary components in the server 200 of FIG. 1, in accordance with aspects of the present disclosure. The server 200 includes, for example, a database 210, one or more processors 220, at least one memory 230, and a network interface 240.

The database 210 can be located in a storage. The term "storage" may refer to any device or material from which information may be capable of being accessed or reproduced, or held in an electromagnetic or optical form for access by a computer processor. "Storage" may be, for example, volatile memory such as RAM, non-volatile memory which permanently hold digital data until purposely erased, such as flash memory, magnetic devices such as hard disk drives, and optical media such as a CD, DVD, Blu-ray disc, or the like.

In one exemplary aspect of the present disclosure, a web interface can run on the server 200, where the interface includes a scheduling application. In various embodiments, data may be stored on the server 200, including, for example, user tasks, preferences, schedule appointments, historical data, and/or other data. The data can be stored in the server database 210, and sent via the system bus to the processor 220.

As will be described in more detail later herein, the processor 220 executes various processes based on instructions that can be stored in the server memory 230, and utilizing the data from the database 210. With reference also to FIG. 1, a request from a user device, such as a mobile device 140 or a computer 110, can be communicated to the server 200, through the server's network interface 240. For example, a user can conduct scheduling operations on a computer 110. The server 200 can access an operating room's schedule, apply processing to the operating room's schedule, and provide the user with an updated schedule as a result.

The updated schedule may appear though a web interface on the server 200, and the interface can include a scheduling application that the user would see on his computer 110. In various embodiments, push notifications can be sent to a browser in mobile devices 140, 160. Users can be notified at the start of each task by way of a push notification. Similarly, users can be notified at the end of a task if another task is not beginning immediately by way of a push notification. In various embodiments, the application can provide a push notice to users to reschedule when the application detects a significant change to a task or to a user's schedule.

Turnaround time for staff at hospitals means different things. For nurses it can mean one patient leaving an operating room to the next patient entering. For surgeons it can mean from the end of one surgery to the beginning of the next surgery. For the housekeeping staff it means from when they finish cleaning an operating room to when they start cleaning an operating room. All of these various turnaround times have an associated cost in wasted hours. Improving turnover time is a major opportunity to increase a hospital's productivity and reduce costs.

A manager, for example a nurse, will run the floor. Typically a turnover process includes the surgeon completing the surgery, anesthesia cleaning equipment and completing the anesthesia process, and nursing completing charts. Then the patient leaves the room, and the nurses begin to breakdown the room. The housekeeping staff enters and cleans the room. Often requiring at least a 5 minute time period for the chemicals to disinfect the room. Next the room is set up for the next surgery, and the next patient then enters the room. Initial patient prep begins by nursing and anesthesia. The surgeon then scrubs in, and enters room. Anesthesia begins induction and then the surgery commences. Many of these activities happen sequentially instead of in parallel. So when any one of the staff is late, it delays the remaining staff and decreases productivity and increases hospital costs. Currently many hospitals use an all verbal system, and if there are several operating rooms involved this can require coordinating more than a hundred people with various functions.

Accordingly, the disclosure of systems and methods for managing in an efficient manner the turnover of hospital operating rooms is desired.

During operating room turnover, housekeeping utilizes chemicals and a period of "dry time" is used to insure that the cleaning chemicals kill the various germs in the room. Generally, hospital staff is not allowed to enter into the operating room during "dry time". In another embodiment, the systems and methods can automatically lock the door of the operating room during the "dry time," or have an electronic sign that lets the teams know that it is "dry time," and not to enter. Tasks are associated with time frames. For example, a task may have a time frame of 15 minutes. Tasks also include start times and complete times. For example, the task must start by 9 am and complete by 9:15 am.

Figure 3A:
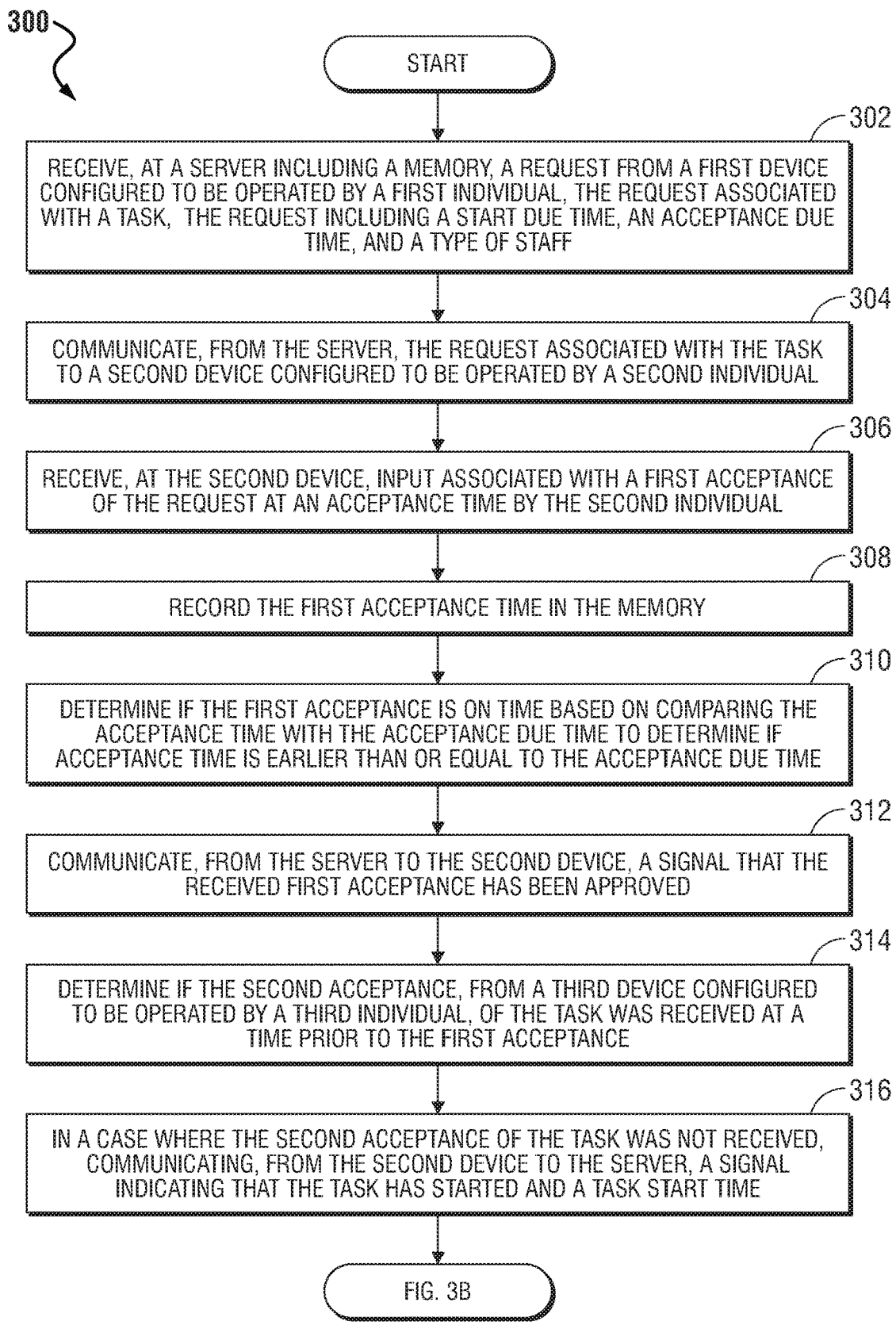
FIG. 3A is an exemplary flow chart of a method for managing in an efficient manner the turnover of hospital operating rooms in accordance with aspects of the present disclosure.

With reference to FIGS. 3A and 3B, the flow diagrams include various blocks described in an ordered sequence. However, those skilled in the art will appreciate that one or more blocks of the flow diagram may be performed in a different order, repeated, and/or omitted without departing from the scope of the present disclosure. The below description of the flow diagram refers to various actions or tasks performed by one or more systems 100, but those skilled in the art will appreciate that the system 100 is exemplary. In various embodiments, the disclosed operations can be performed by another component, device, or system. In various embodiments, the system 100 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the present disclosure.

Referring now to FIGS. 3A and 3B, there is shown an operation for the managing in an efficient manner the turnover of hospital operating rooms. In various embodiments, the operation of FIGS. 3A and 3B can be performed by the system 100 as described herein.

In an embodiment in accordance with the present disclosure, the system for managing hospital operating room turnover may include mobile devices, a mobile application, one or more servers, and users such as hospital operating room staff. The staff can include housekeeping, maintenance personnel, nursing, nursing assistants, anesthesiologist, or surgeon(s), or any other team involved in the operating room. The application may run on the mobile devices which are used by the users to interact with the system.

Figures 4, 5:
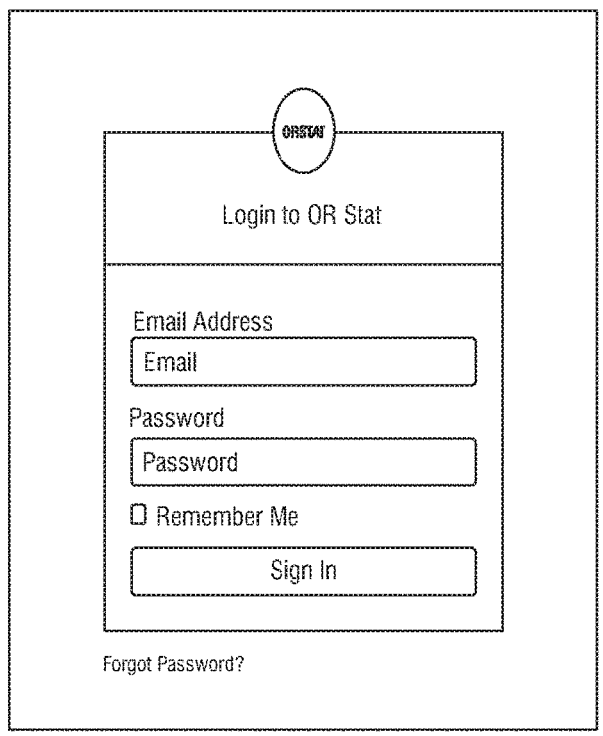
FIG. 4 is an exemplary login view in accordance with aspects of the present disclosure.
FIG. 5 is an exemplary turnover view in accordance with aspects of the present disclosure.
Figure 6:
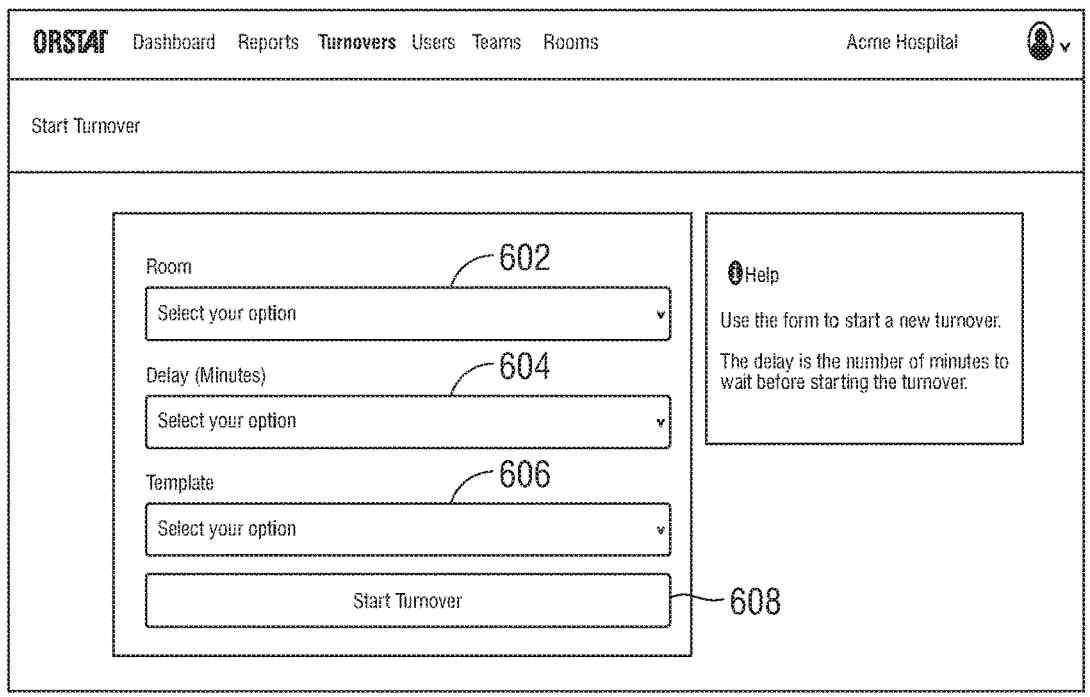
FIG. 6 is an exemplary start turnover view in accordance with aspects of the present disclosure.

Initially at step 302, the server 200 may receive a request from a first device. The first device may be, for example a mobile device 140, 160 or a computer 110, 120 configured to be operated by a first individual, for example the manager of the operating room. In an aspect of the present disclosure, the request may be associated with a task, for example, preparing the operating room by cleaning up after the previous operation. In various embodiments, the request may include a start due time, an acceptance due time, a type of staff, a quantity of staff, and a room identifier. For example, the task may include items such as for housekeeping to clean the room, for surgery to get the patient, or for the nursing assistants or anesthesiology to set up the room at a start due time of 9 am, with an acceptance due time of 8:50 am. With reference to FIGS. 4 and 6, the manager may log into the system 100 and select the operating room with which to start a turnover. In various embodiments, the manager may select the operating room from a dropdown menu. In various embodiments, the manager may enter a delay based on a drop down menu. In various embodiments, the manager may select a delay time for the operating room turnover. In various embodiments, the request may be associated with a predetermined number of unique tokens.

Next at step 304, the server 200 communicates the request associated with the task to a second device configured to be operated by a second individual, such as member of the housekeeping staff or a nurse. For example, the second device may be the mobile device 140, 160 operated by the member of the housekeeping staff or the nurse. In various embodiments, the mobile device 140, 160 may prompt the second individual for an input such as an acceptance or a rejection of the task. For example, a user such as a nurse will get a request on the mobile device, at a predetermined time before the start time (e.g., 10 minutes before), to start a task such as breakdown the room at 9 am.

Next at step 306, the second individual may accept or reject the request by entering the acceptance or rejection on the mobile device 140, 160. In various embodiments, the input associated with acceptance of the request may include an acceptance time. In various embodiments, multiple staff members may be needed for a particular task, for example two or three nurses may be needed for the task. It is contemplated that multiple acceptances may be received by the server 200, each associated with an acceptance time. For example, the nurse may accept this task on the mobile device by clicking a button in the mobile application.

In various embodiments, the server 200 may determine if the received first acceptance is associated with one of the predetermined number of unique tokens. In various embodiments, the server 200 may associate the first received acceptances that are within the number needed for the task with one of the predetermined number of unique tokens.

At step 308, the server 200 records the acceptance time in the memory. Next at step 310, the server 200 determines if the first acceptance is on time based on comparing the acceptance time with the acceptance due time to determine if acceptance time is earlier than or equal to the acceptance due time. In various embodiments, if the acceptance time is not on time, the server 200 records the amount of time that the acceptance was late by. In another aspect of the present disclosure, if the server 200 determines that the task is not accepted on time, it may communicate a late warning to one or more users. For example, on the nurse's mobile device 140, 160 a button may turn red after the system 100 has determined that the time for accepting has passed. In various embodiments, if the time for accepting has passed, the system 100 will notify the nurse through a mobile application on the nurse's mobile device 140, 160.

Next at step 312, the server 200 communicates to the second device, a signal that the received first acceptance has been approved. In various embodiments, the server 200 may associate the one of the predetermined number of unique tokens with the signal that the first acceptance has been approved. In various embodiments, if the number of tokens associated with the task exceeds the predetermined number, the server may communicate a message to the second device that there are enough users assigned to the task Next at step 314, the server 200 determines if a second acceptance, from a third device configured to be operated by a third individual, of the task was received at a time prior to the first acceptance.

Next at step 316, if the second acceptance of the task was not received, from the second device may communicate to the server 200, a signal indicating that the task has started and a task start time. Next at step 318, the server 200 records the start time in the memory. In various embodiments, where it is determined that the task is not started on time, the server may communicate a late warning to the first device and the second device, and recording in the memory that the task is started late. In various embodiments, where it is determined that the task is not accepted on time, the server 200 may communicate to the second device a late warning. For example, when the nurse begins breakdown of the operating room, he/she may click on the appropriate start button in the application running on a mobile device 140, 160 to communicate to the server 200 that the task has started. If for example, the nurse started at 9:05 am, the mobile app may notify the nurse that they started late and will report this to the server 200.

In various embodiments, the system 100 may include an electronically operated lock on the operating room to prevent people from entering, for example during "dry time." In various embodiments, the server 200 may unlock the electronically operated lock after the task start time and/or after staff accepts the task. For example, if the operating room turnover for room 1 has a start time of 10:00 am and three people on the housekeeping staff have accepted, then the server 200 may unlock the electronically operated lock on operating room 1.

Next at step 320, the server 200 determines if the acceptance is on time, the determining including comparing the task start time with the start due time to determine if the task start time is earlier than or equal to the task start due time Next at step 322, the second device may transmit, to the server 200, a signal indicating that a task is complete based on input by the second individual. Next at step 324, based on the signal in step 322, the server 200 records completion of the task. For example, once the task is completed, the nurse can click on a "complete" button in a mobile application to notify the system 100 of task completion. In various embodiments, where it is determined that the task is not completed on time, the server may communicate a late warning to the first device and the second device, and record in the memory that the task is completed late.

Next at step 326, the server 200 transmits a signal to the first device to indicate availability of an operating room.

In an aspect of the present disclosure, if the server 200 determines that the task is not started on time then communicating a late warning to both the one or more users and one or more administration users, and recording the task as completed late.

In a further aspect of the present disclosure, if it is determined that the task is not accepted on time then communicating a late warning to one or more users In a further aspect of the present disclosure, the method includes reporting on time performance. In an even further aspect of the present disclosure, the method includes reporting room performance. In an aspect of the present disclosure, the method includes reporting individual performance. In an aspect of the present disclosure, the method includes reporting team performance.

Referring now to FIGS. 4-12, there is shown an example operation 1200 for the managing in an efficient manner the turnover of hospital operating rooms. In various embodiments, the operation of FIG. 12 can be performed by the system 100 as described herein.

Initially at step 1202 a nurse begins turnover of an operating room. In various embodiments, the nurse may use a mobile device 140, 106, or a computer 110, 120, to initiate room turnover by logging in to the application (FIG. 4) and selecting a room 502 (FIG. 5) and clicking on a start turnover button 504. In various embodiments, the application may have a further screen that allows selection of room 602, delay 604, and a template 606 for the room. (See FIG. 6.) In various embodiments, delay 604 may include the number of minutes to wait before starting the turnover. The delay 604, for example may be ten minutes. The template 606 may include, for example the type of staff needed to turnover the operating room. The nurse then may click on the start turnover button 608.

Figure 11A:
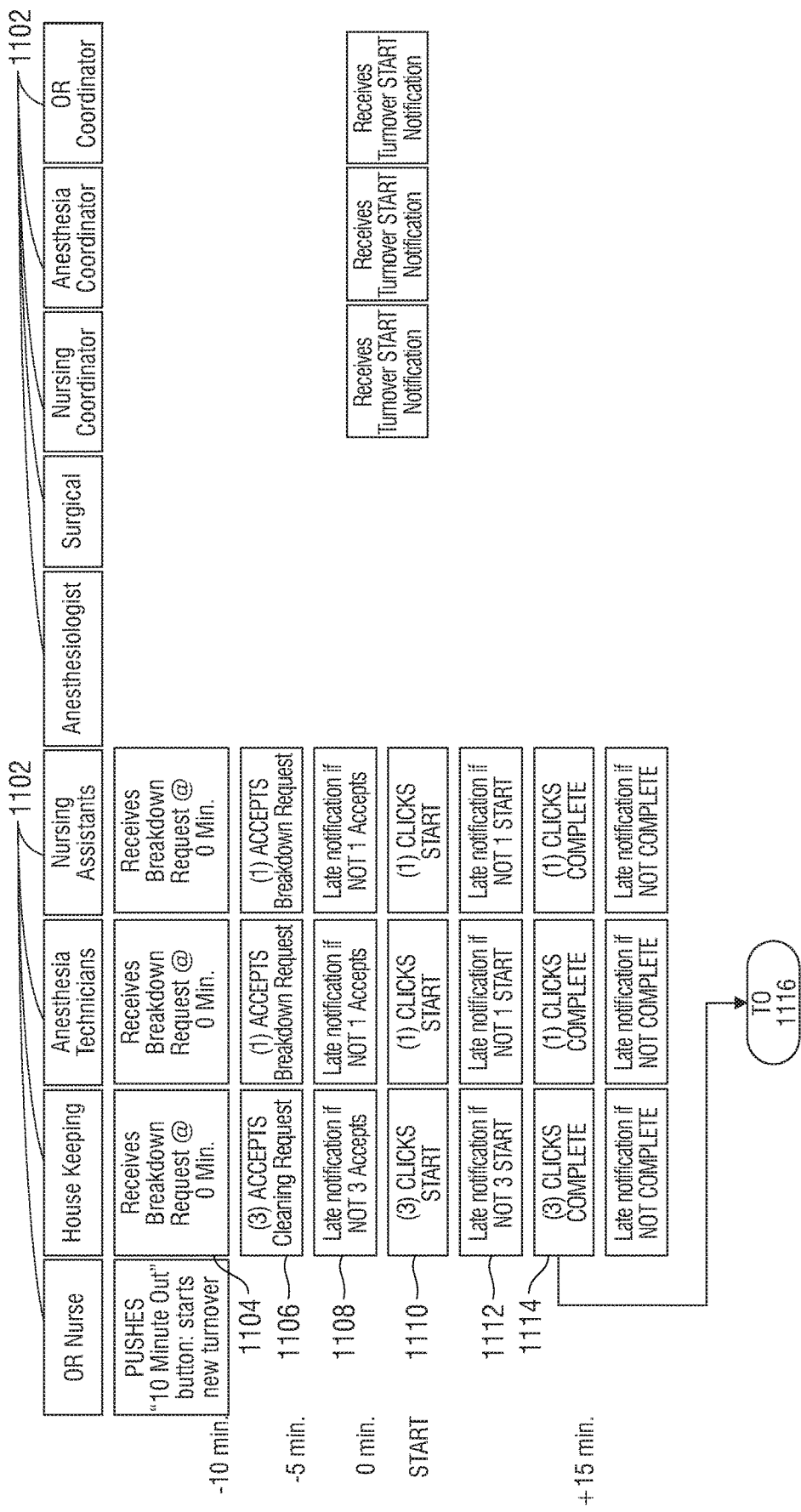
FIGS. 11A and 11B are exemplary process maps in accordance with aspects of the present disclosure.
Figure 11B:
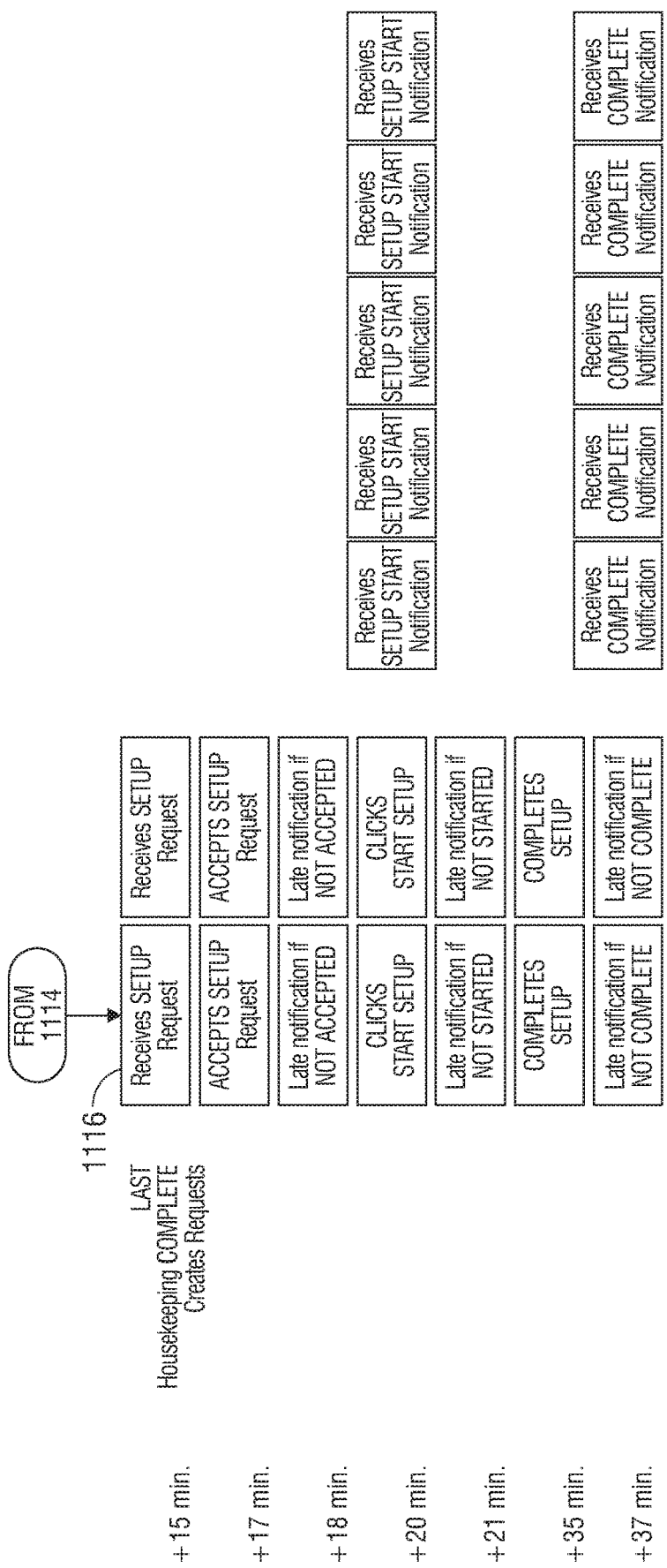

Next at step 1204, the system 100 transmits the tasks associated with the room to user devices. In various embodiments, this notifies the users as to what types of hospital personnel may be needed for a room turnover. With reference to FIG. 11A, the various hospital personnel 1102 may receive a request. For example, a housekeeper may receive a cleaning request 1104.

Figure 12:
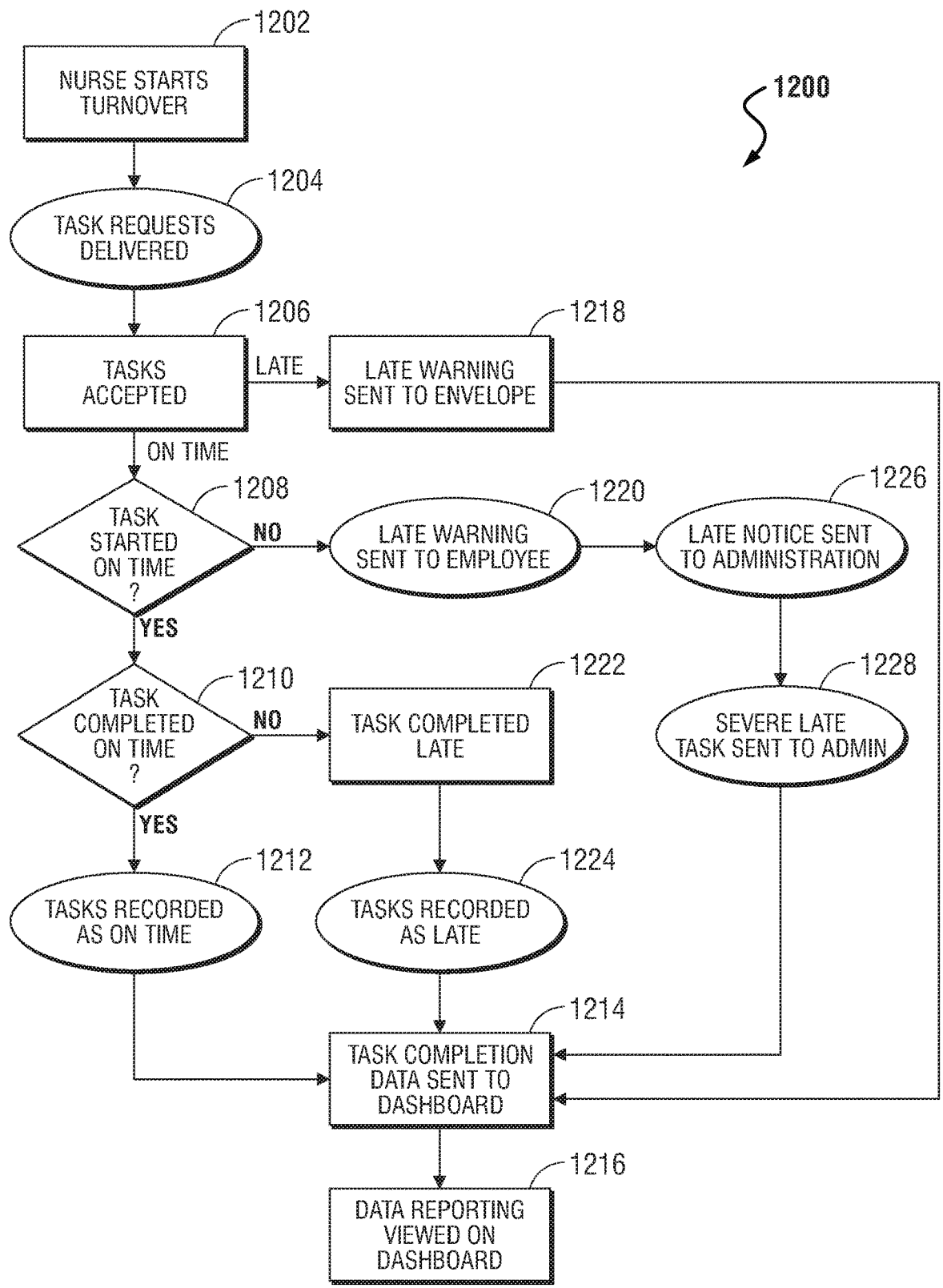
FIG. 12 is an exemplary flow chart of a method for managing in an efficient manner the turnover of hospital operating rooms in accordance with aspects of the present disclosure.

With continued reference to FIG. 12, the tasks are accepted by a user on a mobile device 140, 106. The mobile device 140, 106 may then transmit the acceptance to the system 100. The acceptance may be either late or on time. If the acceptance is late, then next at step 1218 a late warning may be sent to the employee. In various embodiments, this late warning may also be transmitted by the system 100 to the dashboard at step 1214, where it is viewable for data reporting at step 1216. In various embodiments, the system 100 may have a predetermined amount of time stored to determine whether a task is late. For example, if a user accepts a task at approximately 10 minutes before the task start time, then they may be deemed on time. (See FIG. 11A.) Where, for example, if a user accepts a task at approximately 5 minutes before the task start time, then they may be deemed as accepting late. In various embodiments, staff who record a turnover task as "late" can included comments as to why they were late; i.e. excessive dirt, late previous tasks, etc. In various embodiments, a web portal used by management may produce reports on the most used excuse as well as charts comparing excuse use to one another.

If the acceptance is on time, then at step 1208 the system determines whether the task has started on time. If the task has begin late, then next at step 1220 a late warning may be sent to the employee and at step 1226 a late warning may be sent to the administration. In various embodiments, this late warning may also be transmitted by the system 100 to the dashboard at step 1214, where it is viewable for data reporting at step 1216. At step 1226, if the task has begun extremely late, as determined by settings in the system 100, a severe late task notice is sent to the administration. In various embodiments, this may allow the administration to examine why the lateness is so severely late, allowing the administration to remediate any issues.

Next at step 1210 the system determines whether the task was completed on time. In various embodiments, the system stores how long various tasks should take by which the actual time may be compared to. If at step 1222 the system 100 determines the task is not completed on time, then at step 1224 the system records the task as completed late. If at step 1210 the system 100 determines task is on time, based on the predetermined time stored in the system, then at step 1212 the system 100 records that the task is on time.

Next at step 1214 the task completion data is sent by the system 100 to the dashboard, where it is viewable for data reporting at step 1216. It is contemplated that the above operations are happening for multiple rooms and hospital staff in parallel.

In various embodiments, when certain types of hospital staff complete their task, the system 100 may automatically create a request for the next type of staff to begin their task. For example, the last housekeeping staff complete notification may create a setup request 1116 for anesthesia technicians. (See FIG. 11B.)

In various embodiments, the system 100 may include a web portal for reporting data or for users to interact with the system 100. In various embodiments, the system 100 may measure and record the total time to complete each and every turnover. In various embodiments, a reporting feature in the web portal used by managers may be able to show the total time for turnover going back in time, as well, as produce reports on average turnover time on a daily, weekly, monthly, and yearly timeframe for individual staff, teams and an OR department overall.

In various embodiments, the web portal may show charts comparing actual average turnover time versus target turnover time.

In various embodiments, the system 100 may determine and indicate the geo-location of individual staff so that managers can locate them and communication in person.

Figure 7:
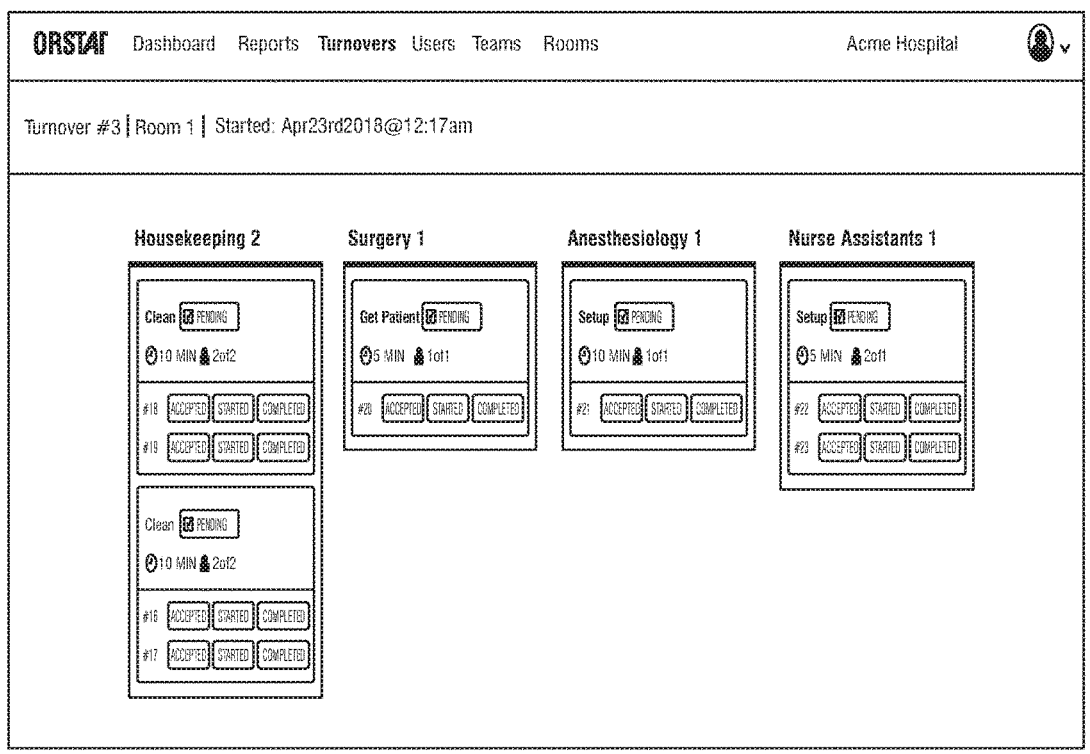
FIG. 7 is an exemplary turnover overview view in accordance with aspects of the present disclosure.
Figure 8:
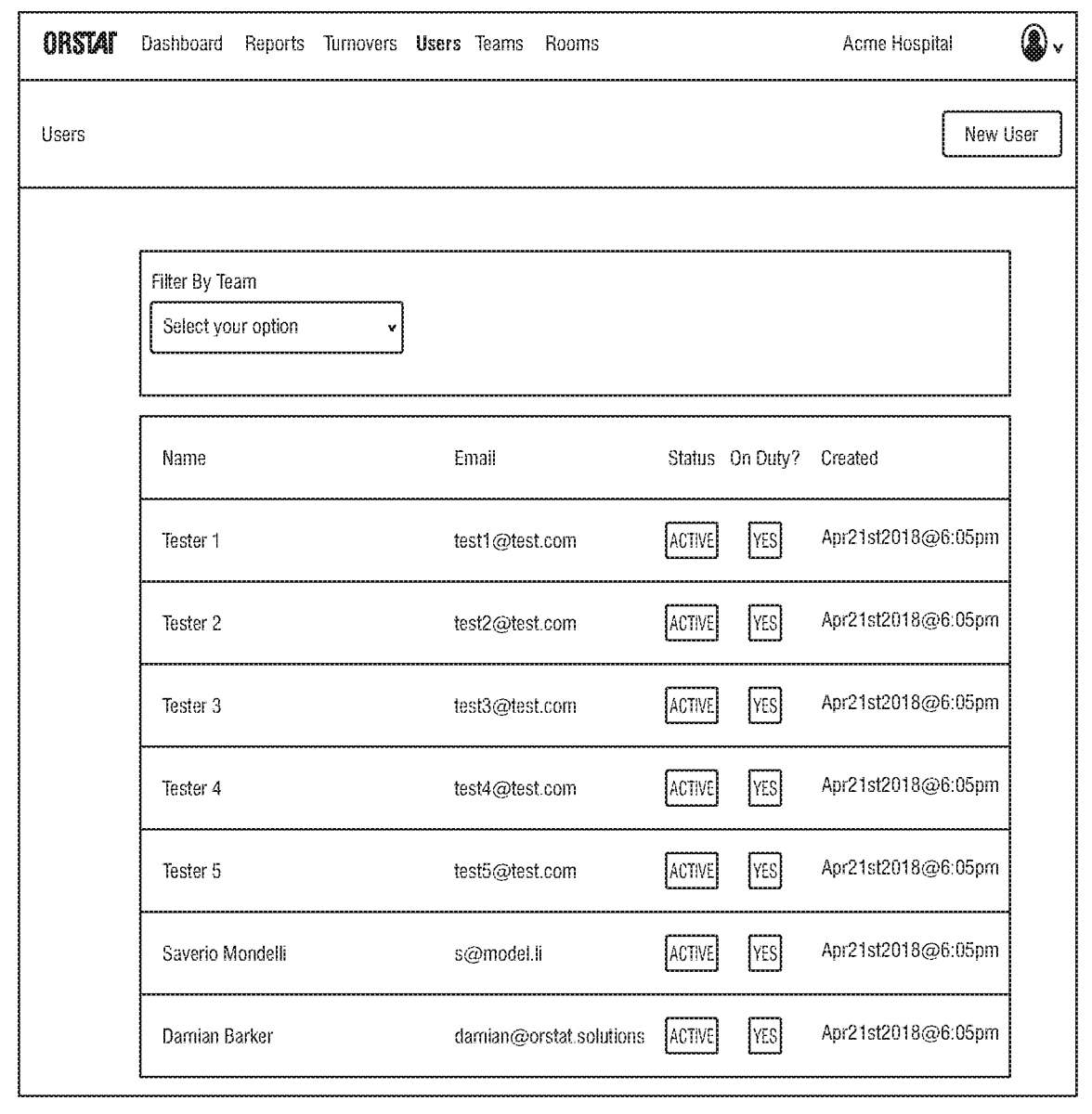

With reference to FIG. 7, in embodiments, the nurse of step 1202 may use the system 100 to get an overview of what tasks have been accepted or completed for what rooms by the staff. With reference to FIG. 8, the nurse of step 1202 may use the system 100 to get an overview of what staff is on duty for the day and whether they are active or not. With reference to FIGS. 9 and 10, the system 100 may include screens for managing the teams and the operating rooms.

In various embodiments, individual staff may be able to check in, start tasks and complete tasks by "waiving" or "swiping" a mobile device in front of hardware installed at the door of each operating room. This may prohibit "cheating" when a staff member could check in as having started a task when they are not actually in an operating room.

In various embodiments, the system 100 may include a chat/text feature that allows managers and staff to communicate directly with each other within the mobile communication app of the present disclosure. In various embodiments, data in the system 100 may be exchanged with other hospital throughput software.

In various embodiments, an artificial intelligence feature may notify management of turnovers that are predicted to be late so that direct human intervention can address excessively late turnovers. In various embodiments, the artificial intelligence may include a neural network. In various embodiments, data from previous turnovers may be used as training data for the neural network. In various embodiments, the training may be supervised or unsupervised. In various embodiments, the output of the neural network may include an inference or a prediction of whether a turnover will be late. In various embodiments, the system 100 may provide a notification of this prediction to personnel, such as supervising staff or administration.

A system of one or more computers and/or mobile devices can be configured to perform particular operations or actions by virtue of having software, firmware, hardware, or a combination of them installed on the system that in operation causes or cause the system to perform the actions described herein. One or more computer programs can be configured to perform particular operations or actions by virtue of including instructions that, when executed by data processing apparatus, cause the apparatus to perform the actions. Implementations of the described techniques may include hardware, a method or process, or computer software on a computer-accessible medium. The system may include one or more displays.

It is contemplated that various machine learning techniques may be used to optimize operating room utilization, or resource allocation. The term "machine learning" may include, but is not limited to, neural networks, naive Bayes, nearest neighbors, least squares, means, and support vector regression, among other data science and artificial science techniques.

It is contemplated that the methods and systems of the present disclosure may be used for scenarios other than for an operating room or hospital. For example, this system could be utilized for managing resources in a manufacturing environment.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure.

The phrases "in an embodiment," "in embodiments," "in various embodiments," "in some embodiments," or "in other embodiments" may each refer to one or more of the same and/or different embodiments in accordance with the present disclosure.

It should be understood that the description herein is only illustrative of the present disclosure. Various alternatives and modifications can be devised by those skilled in the art without departing from the disclosure. Accordingly, the present disclosure is intended to embrace all such alternatives, modifications and variances. The embodiments described are presented only to demonstrate certain examples of the disclosure. Other elements, steps, methods, and techniques that are insubstantially different from those described above and/or in the appended claims are also intended to be within the scope of the present disclosure.

What is claimed is:

1. A computer-implemented method of managing hospital operating room turnover, the method comprising:

receiving, at a server including a memory, a request from a first device configured to be operated by a first individual, the request associated with a task, the request including a start due time, an acceptance due time, and a type of staff, wherein the request includes a delay time for the operating room turnover, the request associated with a predetermined number of unique tokens, wherein the type of staff includes at least one of housekeeping, maintenance personnel, nursing, nursing assistants, anesthesiologist, or surgeon;

communicating, from the server, the request associated with the task to a second device configured to be operated by a second individual;

receiving, at the second device, input associated with a first acceptance of the request at a first acceptance time by the second individual;

recording the first acceptance time in the memory;

automatically unlocking an electronic lock of a door of an operating room, based on the first acceptance;

determining if the first acceptance is on time based on comparing an acceptance time with the acceptance due time to determine if acceptance time is earlier than or equal to the acceptance due time;

communicating, from the server to the second device, a signal that the received first acceptance has been approved;

associating a unique token with the task in response to the signal that the first acceptance has been approved;

determining if a second acceptance, from a third device configured to be operated by a third individual, of the task was received at a time prior to the first acceptance;

determining that a quantity of tokens associated with the task exceeds the predetermined number and communicating a message to the third device that there are enough users assigned to the task based on the determination;

in a case where the second acceptance of the task was not received, communicating, from the second device to the server, a signal indicating that the task has started and a task start time;

recording the task start time in the memory;

determining, at the server, if the first acceptance or the second acceptance is on time, the determining including comparing the task start time with the start due time to determine if the task start time is earlier than or equal to the task start due time;

determining a completion of a task based on receiving a task completion from a plurality of staff;

transmitting, from the second device, a signal indicating that the task is complete based on the determination;

automatically locking the electronic lock of the door of the operating room, based on an end of a "dry time", wherein the "dry time" includes a predefined period of time where the operating room is cleaned by chemicals;

recording, at the server, completion of the task based on the signal indicating that the task is complete; and transmitting, from the server, a signal to the first device to indicate availability of the operating room.

2. The method of claim 1, further comprising, in a case where it is determined that the task is not started on time, communicating a late warning to at least one of the first device and the second device, and recording in the memory that the task is started late.

3. The method of claim 1, wherein if it is determined that the task is not accepted on time, communicating to at least the second device a late warning.

4. The method of claim 1, further comprising calculating on time performance and reporting to a display the on time performance.

5. The method of claim 1, further comprising calculating room performance and reporting to a display the room performance.

6. The method of claim 1, further comprising calculating individual performance and reporting to a display the individual performance.

7. The method of claim 1, further comprising calculating a time to complete the task and reporting to a display the time to complete the task.

8. The method of claim 1, further comprising:
determining a geo-location of individual staff; and
providing an indication of the geo-location of the individual staff.

9. A non-transitory computer-readable storage medium which stores a program causing a computer to execute a computer-implemented method of managing hospital operating room turnover, the computer-implemented method comprising:

receiving, at a server including a memory, a request from a first device configured to be operated by a first individual, the request associated with a task, the request including a start due time, an acceptance due time, and a type of staff, wherein the request includes a delay time for the operating room turnover, the request associated with a predetermined number of unique tokens, wherein the type of staff includes at least one of housekeeping, maintenance personnel, nursing, nursing assistants, anesthesiologist, or surgeon;

communicating, from the server, the request associated with the task to a second device configured to be operated by a second individual;

receiving, at the second device, input associated with a first acceptance of the request at a first acceptance time by the second individual;

recording the first acceptance time in the memory;

automatically unlocking an electronic lock of a door of an operating room, based on the first acceptance;

determining if the first acceptance is on time based on comparing an acceptance time with the acceptance due time to determine if acceptance time is earlier than or equal to the acceptance due time;

communicating, from the server to the second device, a signal that the received first acceptance has been approved;

associating a unique token with the task in response to the signal that the first acceptance has been approved;

determining if a second acceptance, from a third device configured to be operated by a third individual, of the task was received at a time prior to the first acceptance;

determining that a quantity of tokens associated with the task exceeds the predetermined number and communicating a message to the third device that there are enough users assigned to the task based on the determination;

in a case where the second acceptance of the task was not received, communicating, from the second device to the server, a signal indicating that the task has started and a task start time;

recording the task start time in the memory;

determining, at the server, if the first acceptance or the second acceptance is on time, the determining including comparing the task start time with the start due time to determine if the task start time is earlier than or equal to the task start due time;

determining a completion of a task based on receiving a task completion from a plurality of staff;

transmitting, from the second device, a signal indicating that the task is complete based on the determination;

automatically locking the electronic lock of the door of the operating room, based on an end of a "dry time", wherein the "dry time" includes a predefined period of time where the operating room is cleaned by chemicals;
recording, at the server, completion of the task based on the signal indicating that the task is complete; and
transmitting, from the server, a signal to the first device to indicate availability of the operating room.

10. The non-transitory computer-readable storage medium of claim 9 which stores a program causing a computer to execute a computer-implemented method, the computer-implemented method further comprising, in a case where it is determined that the task is not started on time, communicating a late warning to at least one of the first device and the second device, and recording in the memory that the task is started late.

11. The non-transitory computer-readable storage medium of claim 9 which stores a program causing a computer to execute a computer-implemented method, the computer-implemented method further comprising, in a case where it is determined that the task is not accepted on time, communicating to at least the second device a late warning.

12. The non-transitory computer-readable storage medium of claim 9 which stores a program causing a computer to execute a computer-implemented method, the computer-implemented method further comprising calculating on time performance and reporting to a display the on time performance.

13. The non-transitory computer-readable storage medium of claim 9 which stores a program causing a computer to execute a computer-implemented method, the computer-implemented method further comprising calculating room performance and reporting to a display the room performance.

14. The non-transitory computer-readable storage medium of claim 9 which stores a program causing a computer to execute a computer-implemented method, the computer-implemented method further comprising calculating individual performance and reporting to a display the individual performance.

15. The non-transitory computer-readable storage medium of claim 9 which stores a program causing a computer to execute a computer-implemented method, the computer-implemented method further comprising calculating a time to complete the task and reporting to a display the time to complete the task.

16. The non-transitory computer-readable storage medium of claim 9 which stores a program causing a computer to execute a computer-implemented method, the computer-implemented method further comprising:
predicting based on a neural network whether a turnover will be late; and
providing a notification of the prediction.

17. A system for managing hospital operating room turnover, the system comprising:
a first device configured to be operated by a first individual;
a second device configured to be operated by a second individual; and
a server including:
a processor; and
a memory coupled to the processor and having instructions stored thereon which, when executed by the processor, causes the system to:
receive, a request from the first device, the request associated with a task, the request including a start due time, an acceptance due time, and a type of staff, wherein the request includes a delay time for the operating room turnover, is the request associated with a predetermined number of unique tokens, wherein the type of staff includes at least one of housekeeping, maintenance personnel, nursing, nursing assistants, anesthesiologist, or surgeon;
communicate the request associated with the task to the second device;
receive, at the second device, input associated with a first acceptance of the request at a first acceptance time by the second individual;
record the first acceptance time in the memory;
automatically unlock an electronic lock of a door of an operating room, based on the first acceptance;
determine if the first acceptance is on time based on comparing an acceptance time with the acceptance due time to determine if acceptance time is earlier than or equal to the acceptance due time;
communicate, from the server to the second device, a signal that the received first acceptance has been approved;
associate a unique token with the task in response to the signal that the first acceptance has been approved;
determine if a second acceptance, from a third device configured to be operated by a third individual, of the task was received at a time prior to the first acceptance;
determine that a quantity of tokens associated with the task exceeds the predetermined number and communicating a message to the third device that there are enough users assigned to the task based on the determination;
in a case where the second acceptance of the task was not received, communicate, from the second device to the server, a signal indicating that the task has started and a task start time;
record the task start time in the memory;
determine if the first acceptance time or the second acceptance is on time, the determining including comparing the task start time with the start due time to determine if the task start time is earlier than or equal to the task start due time;
determine a completion of a task based on receiving a task completion from a plurality of staff;
transmit, from the second device, a signal indicating that the task is complete based on the determination;
automatically lock the electronic lock of the door of the operating room, based on an end of a "dry time", wherein the "dry time" includes a predefined period of time where the operating room is cleaned by chemicals;
record, at the server, completion of the task based on the signal indicating that the task is complete; and
transmit a signal to the first device to indicate availability of the operating room.

18. The system of claim 17, wherein the memory has further instructions stored thereon which, when executed by the processor, causes the system to, in a case where it is determined that the task is not started on time, communicate a late warning to at least one of the first device and the second device, and recording in the memory that the task is started late.

19. The system of claim 17, wherein the memory has further instructions stored thereon which, when executed by the processor, causes the system to, in a case where it is determined that the task is not accepted on time, communicate to at least the second device a late warning.

20. The system of claim 17, wherein the memory has further instructions stored thereon which, when executed by the processor, causes the system to calculate on time performance and reporting to a display the on time performance.

21. The system of claim 17, wherein the memory has further instructions stored thereon which, when executed by the processor, causes the system to calculate room performance and reporting to a display the room performance.

22. The system of claim 17, wherein the memory has further instructions stored thereon which, when executed by the processor, causes the system to calculate individual performance and reporting to a display the individual performance.

23. The system of claim 17, wherein the memory has further instructions stored thereon which, when executed by the processor, causes the system to calculate a time to complete the task and reporting to a display the time to complete the task.

24. The system of claim 17, wherein the memory has further instructions stored thereon which, when executed by the processor, causes the system to:
  predict based on a neural network whether a turnover will be late; and
  provide a notification of the prediction.

\* \* \* \* \*